US00PP27046P2

(12) United States Plant Patent

Klemm et al.

(10) Patent No.: US PP27,046 P2

(45) Date of Patent: Aug. 9, 2016

(54) *PETUNIA* PLANT NAMED 'KLEPH14248'

(50) Latin Name: *Petunia hybrida*
Varietal Denomination: KLEPH14248

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 3 days.

(21) Appl. No.: 14/545,076

(22) Filed: Mar. 23, 2015

(51) Int. Cl.
*A01H 5/02* (2006.01)

(52) U.S. Cl.
USPC ..... Plt./356.23

(58) Field of Classification Search
USPC ..... Plt./356.23
CPC ..... A01H 5/02
See application file for complete search history.

*Primary Examiner* — Kent L Bell

(74) *Attorney, Agent, or Firm* — Barbara Campbell; Bethany R. Roahrig; Cochran Freund & Young, LLC

(57) ABSTRACT

A new *petunia* plant particularly distinguished by having a dark red flower color and a mounding plant habit, is disclosed.

1 Drawing Sheet

Genus and species: *Petunia hybrida.*
Variety denomination: 'KLEPH14248'.

BACKGROUND OF THE NEW PLANT

The present invention comprises a new and distinct variety of *petunia*, botanically known as *Petunia hybrida* and hereinafter referred to by the variety name 'KLEPH14248'. 'KLEPH14248' is a selection from a cross-pollination of the female *petunia* line 'PH-2009-1404', also known as 'KLEPH12216' (unpatented) and the male petunia line SUN SPUN® Red or 'Balspunred' (patent status unknown).

In July of 2010, the proprietary female *petunia* line 'PH-2009-1404' and the proprietary male *petunia* line 'Balspunred' were cross pollinated in Latina, Italy and seeds were obtained. The seeds were sown and plants were grown for evaluation. A plant line was selected in April 2011 in Latina, Italy and named 'KLEPH14248'. In April 2011, 'KLEPH 14248' was first vegetatively propagated by terminal tip cuttings in Latina, Italy. 'KLEPH14248' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Dark red flower color; and
2. A mounding plant habit.

DESCRIPTION OF THE PHOTOGRAPHS

This new *petunia* plant is illustrated by the accompanying photograph, which shows a close-up of a mature flower. The plant is about 3 months-old grown in Stuttgart, Germany in May 2013.

The colors shown are as true as can be reasonably obtained by conventional photographic procedures.

DESCRIPTION OF THE NEW VARIETY

The following detailed descriptions set forth the distinctive characteristics of 'KLEPH14248'. The data which define these characteristics were collected from asexual reproductions carried out in Latina, Italy. Data was collected on twelve-week-old plants grown indoors in Latina, Italy under greenhouse conditions in February 2015. Color references are to The R.H.S. Colour Chart of The Royal Horticultural Society of London (R.H.S.), 5$^{th}$ edition (2007).

Classification:
- *Family.*—Solanaceae.
- *Species.—Petunia hybrida.*
- *Common name.—Petunia.*
- *Variety.*—'KLEPH14248'.

Parentage:
- *Female.—Petunia* line 'PH-2009-1404'.
- *Male.*—Commercial *petunia* line SUN SPUN® Red also known as 'Balspunred'.

Plant:
- *Form.*—Medium growing.
- *Habit.*—Mounding.
- *Height (from top of soil).*—About 7.0 cm.
- *Width (horizontal plant diameter).*—About 17.0 cm.
- *Propagation.*—Terminal tip cuttings.
- *Time to produce a finished flowering plant.*—About 14 weeks in winter under short day conditions, 7 weeks in spring.
- *Time to initiate and develop roots.*—2 to 3 weeks.
- *Root description.*—Moderate density, moderate branching, white roots.

Stems:
- *Average number (basal).*—9.
- *Length of basal branches (from the base of the stem to the tip).*—6.5 cm.
- *Internode length.*—0.2 cm.

*Diameter of branches* (*from midpoint*).—0.4 cm.
*Stem color*.—RHS 144C.
*Anthocyanin*.—Absent.
*Texture*.—Tomentose.

Leaves:
*Arrangement*.—Alternate.
*Length*.—4.0 cm.
*Width*.—1.8 cm.
*Shape*.—Elliptic.
*Apex*.—Narrowly acuminate.
*Base*.—Attenuate.
*Margin*.—Entire.
*Immature and mature leaf color*.—Upper surface: RHS 137B. Lower surface: RHS 146B.
*Texture*.—Upper and lower surfaces: Tomentose.
*Venation pattern*.—Arcuate.
*Venation color*.—Upper surface: RHS 144A. Lower surface: RHS 144B.
*Petioles*.—Length: 0.7 cm to 1.0 cm. Diameter: 0.2 cm. Color: RHS 144D. Texture: Tomentose.

Flower bud:
*Shape*.—Irregular oblong.
*Length*.—5.5 cm.
*Diameter*.—0.7 cm.
*Color at tight bud*.—RHS 59A and RHS 59B.
*Texture*.—Slightly pubescent.

Inflorescence:
*Blooming habit* (*flowering season*).—Permanent flowering during summertime.
*Inflorescence type*.—Cymose.
*Number of flowers per node*.—1.
*Lastingness of individual blooms on the plant*.—7 to 10 days.
*Fragrance*.—Absent.
*Flowers*.—Arrangement: Composed of 5 petals fused at the base. Shape: Diameter (flower face): 6.0 cm. Depth (total length of flower): 7.5 cm. Throat/Funnel: Length: 4.5 cm. Diameter (at opening): About 1.0 cm. Texture: Both inner and outer surfaces: Smooth, glabrous. Color, immature flower: Face/Margin: RHS 45B. Upper surface: RHS 45B. Lower surface: RHS 54A and RHS 54C. Color, mature flower: Face/Margin color: RHS 46B. Upper surface: RHS 46B. Lower surface: RHS 54A and RHS 54C.
*Petals*.—Apex: Mucronate. Base: Fused. Margin: Entire. Strength of waviness: Weak to medium. Degree of lobation: Low.
*Calyx arrangement*.—Actinomorphic, composed of 5 sepals.
*Sepals*.—Color: Upper surface: RHS 137A. Lower surface: RHS 146A. Length: 0.9 cm. Width: 0.2 cm. Shape: Linear. Apex: Acute. Base: Rounded. Margin: Entire. Texture: Upper and lower surfaces: Tomentose.
*Pedicels*.—Color: RHS 137D. Diameter: 0.5 cm. Texture: Tomentose.

Reproductive organs:
*Stamens*.—Quantity: 5. Shape: Needle-like with elliptic head. Filament: Length: 1.2 cm to 1.8 cm. Diameter: 0.01 cm. Color: RHS 145D. Anther: Shape: Elliptic. Color: RHS 150D. Length: 0.25 cm. Diameter: 0.15 cm. Pollen: Color: RHS 10D.
*Pistils*.—Quantity per flower: 1. Stigma color: RHS 145A. Style color: RHS145B.

Fruit and seed set: No fruit and seed set observed.
Disease and pest/insect resistance: None observed.

COMPARISON WITH PARENTAL LINES AND KNOWN VARIETY

'KLEPH14248' is a distinct variety of *petunia*. 'KLEPH14248' is distinguished from its parents as described in Table 1:

TABLE 1

Comparison with Parental Lines

| Trait | Variety 'KLEPH14248' | Female parent 'PH-2009-1404' | Male Parent 'Balspunred' |
|---|---|---|---|
| Plant habit | Mounding | Semi trailing | |
| Flower color | Darker and more stable red than 'Balspunred' | | Red |

'KLEPH14248' is most similar to the commercial *petunia* plant named SUN SPUN® Red also known as 'Balspunred' (patent status unknown). Differences between the two varieties are described in Table 2:

TABLE 2

Comparison with Similar Variety

| Trait | Variety 'KLEPH14248' | Commercial line 'Balspunred' |
|---|---|---|
| Flower color | Darker and more stable red than 'Balspunred' | Red |

We claim:

1. A new and distinct variety of *petunia* plant named 'KLEPH14248' as illustrated and described herein.

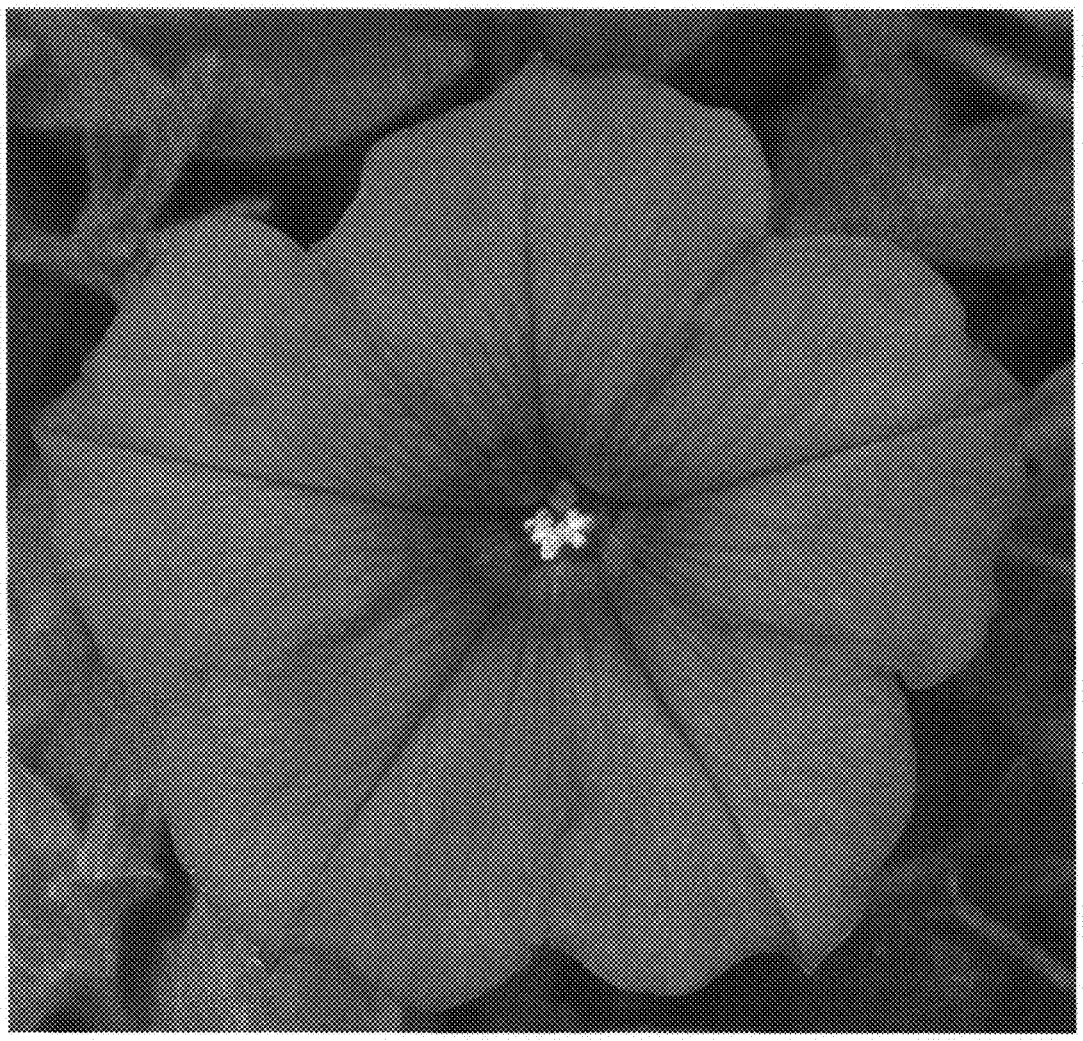

* * * * *